US012194052B2

(12) United States Patent
Savangikar et al.

(10) Patent No.: US 12,194,052 B2
(45) Date of Patent: Jan. 14, 2025

(54) CHLOROPHYLL COMPOSITION

(71) Applicants: Chitra Vasant Savangikar, Maharashtra (IN); Vasant Anantrao Savangikar, Maharashtra (IN)

(72) Inventors: Chitra Vasant Savangikar, Maharashtra (IN); Vasant Anantrao Savangikar, Maharashtra (IN)

(73) Assignees: Chitra Vasant Savangikar (IN); Vasant Anantrao Savangikar (IN)

( * ) Notice: Subject to any disclaimer, the term of this patent is extended or adjusted under 35 U.S.C. 154(b) by 0 days.

(21) Appl. No.: 15/543,966

(22) PCT Filed: Jan. 15, 2016

(86) PCT No.: PCT/IN2016/050017
§ 371 (c)(1),
(2) Date: Jul. 14, 2017

(87) PCT Pub. No.: WO2016/116950
PCT Pub. Date: Jul. 28, 2016

(65) Prior Publication Data
US 2018/0325915 A1 Nov. 15, 2018

(30) Foreign Application Priority Data
Jan. 19, 2015 (IN) .......................... 178/MUM/2015

(51) Int. Cl.
| | |
|---|---|
| *A61K 31/555* | (2006.01) |
| *A61K 9/00* | (2006.01) |
| *A61K 9/48* | (2006.01) |
| *A61K 47/10* | (2017.01) |
| *A61K 47/26* | (2006.01) |
| *A61P 13/12* | (2006.01) |

(52) U.S. Cl.
CPC .......... *A61K 31/555* (2013.01); *A61K 9/0095* (2013.01); *A61K 9/4866* (2013.01); *A61K 47/10* (2013.01); *A61K 47/26* (2013.01); *A61P 13/12* (2018.01)

(58) Field of Classification Search
CPC ...................................................... A61P 13/12
See application file for complete search history.

(56) References Cited

U.S. PATENT DOCUMENTS

| | | | |
|---|---|---|---|
| 2,729,586 A | 1/1956 | Peck | |
| 3,137,632 A | 6/1964 | Schiraldi | |
| 7,887,848 B2* | 2/2011 | Chien ................... | A61K 31/197 424/600 |
| 2008/0139524 A1* | 6/2008 | Bailey ................... | A61K 31/555 514/185 |
| 2008/0317725 A1 | 12/2008 | Baum | |
| 2015/0352189 A1* | 12/2015 | Schentag ............. | A61K 31/155 424/472 |

FOREIGN PATENT DOCUMENTS

| | | |
|---|---|---|
| CN | 1212151 A | 3/1999 |
| CN | 102138919 A1 | 8/2011 |
| CN | 103027873 A | 4/2013 |
| CN | 103285097 A | 9/2013 |
| DE | 4033530 A1 | 4/1992 |
| IN | 102462671 A | 5/2012 |
| JP | S 55161863 A | 12/1980 |
| JP | H 04327534 A | 11/1992 |
| JP | HO4327534 A | 11/1992 |
| JP | 2002003365 A | 1/2002 |
| WO | 2014110090 A1 | 7/2014 |

OTHER PUBLICATIONS

Rule, Using Serum Creatinine To Estimate Glomerular Filtration Rate: Accuracy in Good Health and in Chronic Kidney Disease, Annals of Internal Medicine, 2004, 141(12), pp. 929-937 (Year: 2004).*
Xu Xi et al., "Effects of sodium ferrous chlorophyll treatment on anemia of hemodialysis patients and relevant biochemical parameters", A Biol Regul Homeost Agents, Jan.-Mar. 2016; 30(1): 135-40.
Amnah Mohammed Alsuhaibani et al. Effects of Chlorophyll on Body Functioning and Blood Glucose Levels. Asian Journal of Clinical Nutrition. vol. 9 (2): 64-70, 2017.
Notification of Grant, Date of Issue: Jul. 25, 2018, Patent Journal, vol. 51 No. 07, p. 278 for corresponding South African Patent Application No. 2017/04804.
Certificate of Grant, dated Jan. 24, 2019 for corresponding Australian Patent No. 2016210540.

(Continued)

*Primary Examiner* — Savitha M Rao
*Assistant Examiner* — Andrew P Lee
(74) *Attorney, Agent, or Firm* — MASCHOFF BRENNAN

(57) ABSTRACT

This invention comprises a chlorophyllin composition and method of administering the same for using the same for treatment of kidney disease patients to achieve decrease in serum creatinine level. The chlorophyllin composition and its method of administration is also for concurrent increase in blood hemoglobin level. The Chlorophyllin is selected from the group consisting of sodium copper chlorophyllin, Potassium copper chlorophyllin, Potassium Iron chlorophyllin and other metal containing chlorophyllin/s. To the chlorophyllin composition are added additives, optionally, (a) a diluent, excipient or a carrier, and optionally (b) the chlorophyllin composition is administered, either concurrently, sequentially or in any other order, with other ingredients/compositions supportive for kidney function. The dosage form of composition comprises a liquid, powder, tablet and a capsule. A kit is also provided comprising the chlorophyllin composition and the additional ingredients. The other ingredients comprise amino acids taken individually or as a mixture, protein hydrolysate, proteins or protein concentrates, vitamins and minerals.

16 Claims, No Drawings

(56) References Cited

OTHER PUBLICATIONS

Examination Report, dated Mar. 22, 2019 for corresponding India Application No. 201727022163.
Notice of Office Action, dated Apr. 29, 2019 for corresponding Eurasian Application No. 201791319/28.
Notice of Reason(s) for Rejection, dated Jun. 25, 2019 for corresponding Japanese Application No. 2017-539029.
Breinholt V, Hendricks J, Pereira C, Arbogast D, Bailey G., "Dietary chlorophyllin is a potent inhibitor of aflatoxin B1 hepatocarcinogenesis in rainbow trout", Cancer Res. 1995; 55(1):57-62.
Chernomorsky SA, Segelman AB., "Biological activities of chlorophyll derivatives", N J Med. 1988;85(8):669-673. (PubMed) in "Chlorophyll and Chlorophyllin"; Available online: http://lpi.oregonstate.edu/mic/dietary-factors/phytochemicals/chlorophyll-chlorophyllin.
Dashwood R, Yamane S, Larsen R., "Study of the forces of stabilizing complexes between chlorophylls and heterocyclic amine mutagens", Environ Mol Mutagen. 1996;27(3):211-218.
Dingley KH, Ubick EA, Chiarappa-Zucca ML, et al., "Effect of dietary constituents with chemopreventive potential on adduct formation of a low dose of the heterocyclic amines PhIP and IQ and phase II hepatic enzymes", Nutr Cancer. 2003;46(2):212-221.
Egner PA, Munoz A, Kensler TW, "Chemoprevention with chlorophyllin in individuals exposed to dietary aflatoxin", Mutat Res. 2003;523-524:209-216.
Gao F, Hu XF, "Analysis of the therapeutic effect of sodium copper chlorophyllin tablet in treating 60 cases of leukopenia", Chin J Integr Med. Dec. 2005;11(4):279-82.
Hoelscher, M. et al., "Pharmacological prolongation of ischemic tolerance of rat-kidneys by Na-Cu-chlorophyllin" Transactions—American Society for Artificial Internal Organs (1975) vol. 21 pp. 96 to 101.
JECFA (Joint FAO/WHO Expert Committee on Food Additives), Toxicological evaluation of certain food colours, emulsifiers, stabilizers, anti-caking agents and certain other substances. Chlorophyll copper complex/chlorophyllin/sodium/potassium salts, 1969, WHO Food Additives Series, No. 70.36, No. 135 on INCHEM; Available online: http://www.inchem.org/documents/jecfa/jecmono/v46aje04.htm.
Kamat JP1, Boloor KK, Devasagayam TP; "Chlorophyllin as an effective antioxidant against membrane damage in vitro and ex vivo", BiochimBiophysActa. Sep. 27, 2000;1487(2-3):113-27.
Kephart, John C., Chlorophyll Derivatives—Their Chemistry, Commercial Preparation and Uses, Economic Botany 1955;9:3-38.
Kumar SS, Devasagayam TP, Bhushan B, Verma NC, "Scavenging of reactive oxygen species by chlorophyllin: an ESR study", Free Radic Res. 2001;35(5):563-574.
Kumar SS, Shankar B, Sainis KB, "Effect of chlorophyllin against oxidative stress in splenic lymphocytes in vitro and in vivo", Biochim Biophys Acta. 2004; 1672(2):100-111.
Park KK, Park JH, Jung YJ, Chung WY, "Inhibitory effects of chlorophyllin, hemin and tetrakis(4-benzoic acid)porphyrin on oxidative DNA damage and mouse skin inflammation induced by 12-O-tetradecanoylphorbol-13-acetate as a possible anti-tumor promoting mechanism", Mutat Res. 2003;542(1-2):89-97.
Tachino N, Guo D, Dashwood WM, Yamane S, Larsen R, Dashwood R., "Mechanisms of the in vitro antimutagenic action of chlorophyllin against benzo[a]pyrene: studies of enzyme inhibition, molecular complex formation and degradation of the ultimate carcinogen", Mutat Res. 1994;308(2):191-203.
US FDA, Department US Health Services, Rules and Regulations 21 CFR Part 357 RIN 0905-AA08, "Deodorant Drug Products for Internal Use for Over-the-Counter Human Use; Final Monograph", 19862 Federal Register, vol. 55, No. 82, May 21, 1990.
Yang UJ1, Park TS, Shim SM, "Protective effect of chlorophyllin and lycopene from water spinach extract on cytotoxicity and oxidative stress induced by heavy metals in human hepatoma cells", J Toxicol Environ Health A., 2013;76(23):1307-15. doi: 10.1080/15287394.2013.851632.
Yun CH, Jeong HG, Jhoun JW, Guengerich FP, "Non-specific inhibition of cytochrome P450 activities by chlorophyllin in human and rat liver microsomes", Carcinogenesis. 1995;16(6):1437-1440.
Extended European Search Report, dated May 29, 2018 for corresponding European Application No. 16 73 98 93.
Examination Report, dated Mar. 7, 2018 for corresponding Australian standard patent application No. 2016210540.
International Search Report, mailing date Jul. 18, 2016 for corresponding International Application No. PCT/IN2016/050017.
Written Opinion of ISA, mailing date Jul. 18, 2016 for corresponding International Application No. PCT/IN2016/050017.
Notice of Office Action, dated Apr. 15, 2019 for corresponding European Application No. 16 739 893.2, pp. 1-4.
Search Report, dated Oct. 4, 2019 with Technical Report dated Jan. 28, 2020, for corresponding Brazilian Patent Application No. 11 2017 015338 6, pp. 1-4.
Notice of Office Action, dated Oct. 18, 2019 for corresponding European Application No. 16 739 893.2, pp. 1-5.
Decision as to patentability of the invention, dated Jan. 16, 2020 for corresponding Eurasian Patent Application No. 201791319/28, pp. 1-3.
Notice of Office Action, dated Feb. 3, 2020 for corresponding China Application No. 201680006322.4, pp. 1-8.
Notification of Eligibility for Grant, Dated Feb. 3, 2020 for corresponding Singapore Patent Application No. 11201705694V, pp. 1-1.
Notice of First Office Action, dated Jan. 15, 2020 for corresponding China Application No. 201680006322.4 with English translation, pp. 1-18.
Decision as to patentability of the invention, dated Jan. 16, 2020 for corresponding Eurasian Patent Application No. 201791319/28 with English translation, pp. 1-6.
ARIPO Form 18 with Search Report, dated May 26, 2020 for corresponding Africa Application No. AP/P/2017/010065, pp. 1-5.
Decision of Grant, dated Sep. 1, 2020 for corresponding Japanese Patent Application No. 2017-539029, pp. 1-4 with English translation.
Notice of Second Office Action, dated Sep. 28, 2020 for corresponding China Application No. 201680006322.4 with English translation, pp. 1-19.
Intention to Grant patent, dated Sep. 22, 2020 for corresponding European Patent Application No. 16 739 893.2, pp. 1-30.
The Eurasian Patent Organisation—The Eurasian Patent Office; Decision as to Patentability of the Invention dated Jun. 14, 2022 issued in application No. 201791319, 10 pages.
African Regional Intellectual Property Organization (ARIPO); Notification of Decision to Grant or Register (Form 21 and Addendum) dated Jan. 10, 2022, issued in application No. AP/P/2017/010065; 5 pages.
Ivanova N.A. Development of technology for the production of soft gelatin capsules with hydrophilic fillers by the rotational matrix method. Dissertation for the degree of Candidate of Pharmaceutical Sciences. SBEI HVE Perm State Pharmaceutical Academy, Perm, 2013.
Hoelscher, M. et al. "Pharmacological prolongation of Ischemic tolerance of rat-kidneys by Na-Cu-Chlorophyllin", Transsactions—American Society for Artificial Internal Organs. (1975); vol. 21, pp. 96-101.
Brazil Patent Office Technical Report issued in Application No. BR 112017015338-6 dated Jun. 22, 2023.

* cited by examiner

CHLOROPHYLL COMPOSITION

CROSS-REFERENCE TO RELATED APPLICATIONS

This application is a U.S. National Phase application, under 35 U.S.C. § 371, of International Application no. PCT/IN2016/050017, with an international filing date of Jan. 15, 2016, and claims benefit of India Application no. 178/MUM/2015 filed on Jan. 19, 2015, and which are hereby incorporated by reference for all purposes.

FIELD OF INVENTION

Invention discloses chlorophyllin corn positions, commonly called as "chlorophyll compositions", for human consumption. Invention also discloses chlorophyllin compositions for treatment of kidney disease.

BACKGROUND OF THE INVENTION

Chlorophyllins include a group of closely related water-soluble salts that are semi-synthetic derivatives of chlorophyll, differing in the cations associated with the anion. For the purpose of this specification, the group of chlorophyllins shall be designated as "metal containing chlorophyllin/s". The most commonly used form is sodium copper derivative that comprises Sodium copper chlorophyllin which comprises sodium copper derivative/s of the chlorophyll extracted from green leaves/vegetation/plant material. Potassium copper chlorophyllin and Potassium Iron chlorophyllin are also known and characterized/standardized. Chlorophyllins are generally available as solid powder. Compositions of chlorophyllin, particularly of sodium copper chlorophyllin has been known since a long time for their use as a food color and also for their use as a deodorizer of feces in colostomy and ileostomy patients, for removal of body odor, for removal of urine odor, for wound dressing and for detoxification of carcinogens in the body. Compositions of chlorophyllin are popularly known as "chlorophyll composition". Liquid compositions comprising chlorophyllins are commonly known as ""Liquid Chlorophyll" and are considered as a general wellness/health supplement.

Commercial Sodium copper chlorophyllin available as powder contains highly variable content of Sodium copper chlorophyllin, which clearly indicates that these commercial compositions contain sodium copper chlorophyllin and diluents added to them in varying amounts or non-chlorophyllin ingredients derived from the raw material during the process of extraction of chlorophyll from the raw material prior to converting the chlorophyll into sodium copper chlorophyllin. JECFA [*Prepared at the* 31*st JECFA* (1987), published in the *Combined Compendium of Food Additive Specifications, FAO JECFA Monographs* 1 (2005). *Corrected at the* 69*th JECFA* (2008)] provides chemical formulae of copper chlorophyllin a (acid form) as $C_{34}H_{32}CuN_4O_5$ and of Copper chlorophyllin b (acid form) as $C_{34}H_{30}CuN_4O_6$. The Formula weights are given as Copper chlorophyllin a: 640.20 and Copper chlorophyllin b: 654.18, each may be increased by 18 Daltons if the cyclopentenyl ring is cleaved. Thus, presuming that the cyclopentenyl ring is not cleaved, as derived from these formulae, a 95% pure form shall have 8% copper in Copper chlorophyllin a and in Copper chlorophyllin b. The characterization of the chlrophyllins given by JECFA are for a 95% purity in assay for total chlorophyllin after drying (100°, 1 h).

Compositions for nutraceutical use, popularly known as "Liquid Chlorophyll" and as softgels have come up made by using the solid copper chlorophyllin powder as an ingredient. On account of highly variable purity of the commercially available compositions of chlorophyllin available in the market, unless non-ionic copper content is specified, it is not possible to know the correct content of copper chlorophyllin in commercially available formulations and nothing can be inferred about the properties and specifications of the commercial products available online. However, based on the information available online on the internet and examining the products bought from online sources, the "Liquid Chlorophylls" are a solution or an emulsion of this solid powder made predominantly in water, the solution/emulsification being aided by solubilizers that include oil and a surfactant. Softgels contain a water-in-oil emulsion of sodium copper chlorophyllin, further containing water, oil and glycerol as ingredients.

Liquid Chlorophyll and soft-gels are consumed for their professed health benefits for preventing bad breath, preventing bad body odour or fecal odor or urine odor, preventing constipation, "detoxification," wound healing, anti-bacterial properties, anti-cancer properties by binding carcinogens, forming tight molecular complexes with carcinogens (cancer causing agents) such as in tobacco smoke and in cooked meat. It helps in reducing the activities of enzymes that are responsible for converting normal chemicals into cancer causing agents. It is used as internal deodorant. It was being used as a wound dressing material in 1940s and 1950s to deodorize the effect of foul-smelling wound. It is used for oral administration for people with colostomies and ileostomies (diversion of feces from the colon into a pouch) or incontinence to reduce fecal odor, as an antioxidant to neutralize oxidants and to reduce oxidative damages induced by chemical cancer causing agent or radiation and to boost the immune system. Liquid Chlorophyll has achieved widespread market as a general wellness health supplement.

Recently, methodic scientific work has started appearing in publications which is supporting some of the claims made in the past. Thus, Yang et al (2013) (Yang U J1, Park T S, Shim S M.) showed protective effect of chlorophyllin and lycopene from water spinach extract on cytotoxicity and oxidative stress induced by heavy metals in human hepatoma cells. (J Toxicol Environ Health A. 2013;76(23):1307-15. doi: 10.1080/15287394.2013.851632.). They have shown that Sodium Copper Chlorophyllin might be associated with diminished absorption of metal ions by chelating and blocking metal-mediated generation of Reactive Oxygen Species.

Gao et al (2005) (Gao F, Hu X F. In Chin J Integr Med. 2005 December; 11(4):279-82) have given analysis of the therapeutic effect of sodium copper chlorophyllin tablet in treating 60 cases of leukopenia.

Chlorophyll and chlorophyllins are able to form tight molecular complexes with certain chemicals known or suspected to cause cancer, including polycyclic aromatic hydrocarbons found in tobacco smoke, some heterocyclic amines found in cooked meat, and aflatoxin-$B_1$. The binding of chlorophyll or chlorophyllin to these potential carcinogens may interfere with gastrointestinal absorption of potential carcinogens, reducing the amount that reaches susceptible tissues.

To initiate the development of cancer, some chemicals (pro-carcinogens) must first be metabolized to active carcinogens that are capable of damaging DNA or other critical molecules in susceptible tissues. Since enzymes in the cytochrome P450 family are required for the activation of some pro-carcinogens, inhibition of cytochrome P450 enzymes may decrease the risk of some types of chemically induced cancers. In vitro studies indicate that chlorophyllin may decrease the activity of cytochrome P450 enzymes. Phase II biotransformation enzymes promote the elimination of potentially harmful toxins and carcinogens from the body. Limited data from animal studies indicate that chlorophyllin may increase the activity of the phase II enzyme, quinone reductase.

Tachino et al (1994) state that natural chlorophylls are not known to be toxic, and no toxic effects have been attributed to chlorophyllin despite more than 50 years of clinical use in humans. Several studies on complexes between chlorophylls and mutagens or carcinogens and other aspects of chlorophyll action have been reported [Tachino N, Guo D, Dashwood W M, Yamane S, Larsen R, Dashwood R. Mechanisms of the in vitro antimutagenic action of chlorophyllin against benzo[a]pyrene: studies of enzyme inhibition, molecular complex formation and degradation of the ultimate carcinogen. Mutat Res. 1994; 308(2):191-203.; Dashwood R, Yamane S, Larsen R. Study of the forces of stabilizing complexes between chlorophylls and heterocyclic amine mutagens. Environ Mol Mutagen. 1996; 27(3):211-218.; Breinholt V, Schimerlik M, Dashwood R, Bailey G. Mechanisms of chlorophyllin anticarcinogenesis against aflatoxin B1: complex formation with the carcinogen. Chem Res Toxicol. 1995; 8(4):506-514; Egner P A, Munoz A, Kensler T W. Chemoprevention with chlorophyllin in individuals exposed to dietary aflatoxin. Mutat Res. 2003; 523-524:209-216; Kumar S S, Devasagayam T P, Bhushan B, Verma N C. Scavenging of reactive oxygen species by chlorophyllin: an ESR study. Free Radic Res. 2001; 35(5):563-574; Kamat J P, Boloor K K, Devasagayam T P. Chlorophyllin as an effective antioxidant against membrane damage in vitro and ex vivo. Biochim Biophys Acta. 2000; 1487(2-3):113-127; Park K K, Park J H, Jung Y J, Chung W Y. Inhibitory effects of chlorophyllin, hemin and tetrakis(4-benzoic acid)porphyrin on oxidative DNA damage and mouse skin inflammation induced by 12-O-tetradecanoylphorbol-13-acetate as a possible anti-tumor promoting mechanism. Mutat Res. 2003; 542(1-2):89-97; Kumar S S, Shankar B, Sainis K B. Effect of chlorophyllin against oxidative stress in splenic lymphocytes in vitro and in vivo. Biochim Biophys Acta. 2004; 1672(2):100-111; Yun C H, Jeong H G, Jhoun J W, Guengerich F P. Non-specific inhibition of cytochrome P450 activities by chlorophyllin in human and rat liver microsomes. Carcinogenesis. 1995; 16(6):1437-1440; Dingley K H, Ubick E A, Chiarappa-Zucca M L, et al. Effect of dietary constituents with chemopreventive potential on adduct formation of a low dose of the heterocyclic amines PhIP and IQ and phase II hepatic enzymes. Nutr Cancer. 2003; 46(2): 212-221; Chernomorsky S A, Segelman A B. Biological activities of chlorophyll derivatives. N J Med. 1988; 85(8): 669-673; Kephart J C. Chlorophyll derivative—their chemistry, commercial preparation and uses. Econ Bot. 1955; 9:3-38.]

US FDA (United States Food and Drug Administration) has published a monograph on chlorophyllins for internal use for human being (19862 Federal Register/Vol. 55, No. 82/Friday, May 21, 1990/Rules and Regulations 21 CFR Part 357 RIN 0905-AA08 Deodorant Drug Products for Internal Use for Over-the-Counter Human Use; Final Monograph) and on safety of their use. Accordingly, it is regarded that chlorophyllin as OTC deodorant drug product for internal use are generally regarded as safe for human being above 12 years of age in dosages ranging from 100-300 mg per day in as much divided dosages as possible.

Objective of this invention is to make novel Chlorophyll Compositions. Further objective was to investigate their health benefits.

SUMMARY OF THE INVENTION

This invention comprises a Chlorophyllin composition for use in the treatment of kidney disease patients to achieve decrease in serum creatinine level. This invention also comprises a Chlorophyllin composition for further use to achieve concurrent increase in blood hemoglobin level in kidney disease patient. The Chlorophyllin is selected, one or more, from the group consisting of sodium copper chlorophyllin, Potassium copper chlorophyllin, Potassium Iron chlorophyllin and other metal containing chlorophyllin/s. The composition of the selected chlorophyllin is present in the composition either (a) with a diluent, excipient or a carrier, or (b) without a diluent, exceipient or a carrier. The composition of chlorophyllin may be used either with or without other ingredients/compositions supportive for kidney function, When chlorophyllin is used with other ingredients, either (a) the other ingredient/s are added in the composition itself for facilitating concurrent administration; or (b) the other ingredient/s or the other composition are provided in a kit comprising the composition and the other ingredient/s/composition/s to facilitate separate administration to a patient in need thereof as a part of the kit either sequentially or irrespective of any sequence. The other ingredients are selected from the group consisting of amino acids taken individually or as a mixture, protein hydrolysate, proteins or protein concentrates, vitamins and minerals. The dosage form of composition of this invention is selected from the group consisting of a liquid, powder, tablet and a capsule.

The individual portion of the composition of this invention comprises chlorophyllin, equivalent to 95% pure sodium copper chlorophyllin, 0.01 to 150 mg, more preferably 0.01 to 15 mg, still more preferably 0.01 to 0.2 mg and excipients; wherein the individual portion is 10 ml in case of a liquid composition, one gram in case of a powder composition, one tablet in case of tablet composition and one soft gelatin capsule in case of soft-gel composition.

This invention also comprises a method of treating a patient in need thereof suffering from kidney disease comprising administering the chlorophyllin compositions described above for lowering the level of serum creatinine. The method of this invention of administering chlorophyllin composition comprises further use of this composition to achieve concurrent increase in blood hemoglobin level.

An embodiment of this invention comprises a liquid chlorophyllin composition comprising, per 12.5 gram portion of the composition, chlorophyllin equivalent to 95% pure sodium copper chlorophyllin 0.01 to 150 mg, more preferably 0.01 to 15 mg, still more preferably 0.01 to 0.2 mg, and at least one polyol, and 0 to 3.75 gram of water.

This invention also comprises a soft gelatin capsule comprising chlorophyllin equivalent to 0. 1 to 1.5 milligram of 95% sodium copper chlorophyllin.

DETAILED DESCRIPTION OF THE INVENTION

Decrease in serum creatinine level in a 13 years old girl [case studies (a) in Example 1 described below] was the first surprising indication of a composition of chlorophyllin, Composition 1 described in Example 1 below comprising chlorophyllin being effective for lowering serum creatinine in a Chronic Kidney Disease patient.

This was confirmed subsequently on a diabetic patient of 64 years who had already undergone dialysis three times to bring down his serum creatinine level from 6 to 4.8 turned to get treated with Composition 1 on account of his decision not to continue with any dialysis further on account of the trauma of dialysis. After starting consumption of Composition 1, although no dialysis was performed, his serum creatinine level decreased after 11 days from 4.8 to 3.5. Five days later, he was admitted for angioplasty, for which blood analysis was done again when his serum creatinine was 2.6. This observation indicated, for the first time, an un-expected effect of a chlorophyllin composition for its potential for serum creatinine lowering effect at least as good as the treatment of dialysis; which effect was not known until that time. When this patient stopped taking this composition after the serum creatinine level became normal and he felt relief, the increase in serum creatinine level and accompanying discomfort returned again. Hence, this patient again resumed taking this composition, thereby again leading to drop in serum creatinine level again. This was noted as a very important development since there is no known treatment for Chronic Kidney Disease except dialysis which gives significant decline in serum creatinine within a relatively short time and dialysis itself is a traumatic treatment for most of the patients which gives pretty slow reduction in serum creatinine level, which rises again close to original level or even more than earlier level by the time of next dialysis. Dialysis itself is a traumatic treatment for most patients. Further, it does not lead to an improvement in quality of life, it only helps to maintain slow pace of deterioration and postponement of the adverse event.

This was followed with few more similar such cases which have been reported below in Examples.

Following these observations, above Composition 1 was prescribed to: a group of patients diagnosed for Chronic Kidney Disease but were not willing to go for dialysis for its high cost or were not able to get access to dialysis on account of overbooking for the dialysis machines (Group no. 2 in Table 1). When it was observed that the no-dialysis group started showing decline in serum creatinine even in absence of dialysis, those patients who were taking dialysis also desired to have Composition 1 concurrently, and they were also provided with Composition 1 (Group 1 of Table 1). To group no. 1 as well as 2, Composition 1 was recommended two times a day in first week, once in the morning and once in the evening on empty stomach well in advance of major food consumption; and only once in the morning after the first week and data was kept at monthly intervals for serum creatinine. Concurrently, data was available of the group of patients which received only dialysis (group no. 3 of Table 1), whose monthly data was also kept for serum creatinine. It was observed, that as usual, in group no. 3, serum creatinine levels fluctuated from case-to-case but reduced in third month to some extent. With some exceptions, there was a consistent decrease of serum creatinine in groups 1 and 2, with more decrease in group 2. Record for hemoglobin was available in only some cases. However, in whatever record was available, there was a consistent increase in blood hemoglobin level also in group 1 and 2 patients; and in all dialysis patients of group 3, there was a gradual decline in blood hemoglobin level. Thus, positive contribution of the Composition 1 of this invention was seen in improving clinical parameters of kidney impaired patients. Since serum creatinine levels result was available for all patients the results on serum creatinine were statistically analysed, which proved that the differences in serum creatinine levels of the three groups noted above are highly significant at $P=0.01$.

No remedy was known so far that would be as efficacious as or more than dialysis, including hemodialysis or peritoneal dialysis, for achieving decrease in serum creatinine level for the Chronic Kidney Disease patients at least as much as achieved by dialysis. Thus, there was no efficacious alternative known for dialysis for Chronic Kidney Disease patients. Dialysis treatment is expensive, invasive, a surgical treatment having its own risks and long term complications, and also is traumatic for most of the patients. Thus, there was a long standing problem which has been solved by the compositions of the present invention. Composition of this invention is illustrated by Composition 1 by providing statistically significant more decline in serum creatinine in the patients given the Composition 1 when compared to the reduction in serum ceratinine level patients receiving dialysis treatment.

Record of blood hemoglobin was available for a few patients in dialysis group and group consuming Composition 1. In patients who were on dialysis, blood hemoglobin declined in all cases slowly; which is consistent to the knowledge that with progressive deterioration in the kidneys, erythropoietin production declines leading to drop in hemoglobin levels leading finally to anemia. Dialysis can, of course, do nothing to slow down or reverse this decline in production of erythropoietin. However, surprisingly, in all cases who were administered Composition 1 and record of blood hemoglobin was available, concurrent to decline in serum creatinine, the blood hemoglobin also improved. This indicates that at least a part of kidneys that have lost normal function respond to Chlorophyllin by restoring normal function to a notable extent. Thus, this invention also comprises a chlorophyll composition for a further use to achieve concurrent increase in blood hemoglobin level; concurrent to reduction in serum creatinine. In cases receiving Composition 1, there were a couple of cases who were irregular in consuming Composition 1; and it was notable that their hemoglobin level improved with start of consumption of Composition 1, whenever they discontinued the Composition 1 the hemoglobin level fell and it was restored again when they restarted consuming Composition 1. Considering the individual variations and other confounding factors which differ from person to person and may prevent effect of Composition 1 getting reflected in increase in hemoglobin, it may be exceptionally possible that blood hemoglobin level may not concurrently rise in a Chronic Kidney Disease patient; however, the indications of the data available so far makes it reasonable to conclude that number of such cases may remain very low and at least majority of patients of Chronic Kidney Disease shall show reduction in serum creatinine level concurrent to improvement in blood hemoglobin level if effective quantity of Composition 1 is consumed by them. It may be noted that dialysis is useful only for removing metabolic waste products from the blood, but hemoglobin keeps on declining and becomes one of the risk factors in course of time for the patients receiving dialysis only, which needs to be handled separately through other treatments, including erythropoietin plus iron supplementation treatment, concurrent to administration of iron either orally or parenterally.

It is an embodiment of this invention that for the first time a composition is available for treatment of chronic kidney disease patients for achieving lowering of serum creatinine at least as much as achievable by dialysis concurrent to improvement in blood hemoglobin level.

The composition illustrated herein comprises liquid composition of sodium copper chlorophyllin. However, it may also be possible to use any other metal derivative of chlorophyllin, including without limitation, potassium copper chlorophyllin and Potassium Iron chlorophyllin instead of sodium copper chlorophyllin, and instead of liquid composition the same may be in the form of a tablet, a powder or a capsule also.

Decrease in serum creatinine concurrent to improvement in hemoglobin level does indicate probability of at least some reversal of the damage to the kidneys. Hence, it is possible to expect a further improvement if other ingredients/compositions that are supportive for kidney function and cell membranes are added to this composition or administered separately in sequential manner or in any other manner that is consistent with the nature of and mechanism of action of the other ingredients and their interaction with the chlorophyllin ingredient of the composition. When envisaged for separate administration, a kit may be prepared comprising the composition of chlorophyllin and the other ingredients/compositions provided with written instructions on how and when to administer them to the patient. The other ingredients may include, without limitation, amino acid/s, proteins and protein hydrolysates, vitamins and minerals. The amino acid/s may be one or a mixture of one or more amino acids, the amino acids may preferably comprise essential amino acids. The proteins and protein hydrolysates may preferably be high Biological value dietary protein and the protein hydrolysates may be made from high Biological Value dietary proteins.

This invention, for the first time, has provided a method for treatment of kidney disease patients with an oral composition for achieving reduction in serum creatnine with concurrent improvement in blood hemoglobin.

Compositions have been prepared that have one or more additive/s as an other ingredient in addition to sodium coppered chlorophyll that improves kidney function or supports further improvement in clinical parameters of a kidney patient, such as for supporting improvement of hemoglobin also and/or to provide dietary proteins. The dietary proteins provided may, preferably, have high Biological Value.

The said other ingredient/additive/composition may be one that comprises at least one fraction of a green leafy vegetation and at least one more ingredient to improve its usability, 100 gram of the composition on dry weight basis comprising at least one nutritional ingredient being selected from the group (a) beta carotene at least 500 microgram, (b) iron at least 3 mg, (c) calcium at least 150 mg, (d) xanthophylls at least 4 mg, (e) folic acid at least 35 microgram, and (f) lysine at least 900 mg and Methionine plus cystine at least about 550 mg; wherein the fraction comprises first three primary fractions as well as sub-fraction or a modified fraction of the three primary fractions of the green leafy vegetation; the primary fraction being obtained in a process of green crop fractionation, wherein the fractionation process comprises the steps of: (i.) comminuting fresh green crop material, (ii.) separating a moist fibrous fraction as first primary fraction from the juice as second primary fraction, and treating the juice fraction to separate a water soluble deproteinized juice that is high in water content as third primary fraction from a water insoluble high protein low fiber fraction as fourth primary fraction. These primary fractions may either be microbiologically stabilized before use as an ingredient in a dry mix or they are wet processed to make high moisture compositions, packaged and the packages are microbiologically stabilized either by sterilizing at 120° C. under a pressure of 15 pounds per square inch for at least 20 minutes, or by adding permitted preservatives or deep freezing below 0° C. to up to −40° C. or by expelling moisture until moisture content of the composition is below 10% up to 5%.

The additional other ingredient/additive/composition may also be a dietary protein. The dietary protein may preferably be chosen from a high Biological Value dietary protein. The term "Biological Value" indicates percentage of dietary protein that is retained in the body of the protein absorbed in the digestive tract. Egg protein is a dietary protein that has highest Biological Value i.e. 100%. This is followed by "water insoluble high protein low fiber fraction" mentioned above, milk protein and whey protein, which have Biological Value of about 85% or more; and are considered as high Biological value dietary proteins.

The additional other ingredient/additive/composition may also be a hydrolyzate of a protein. The hydrolyzate may preferably and enzymatic hydrolyzate and still further an enzymatic hydrolyzate of high Biological Value dietary protein.

The additional other ingredient/additive/composition may also be amino acids or mixture of amino acids, The amino acid may comprise one or more of essential amino acids.

The additional other ingredient/additive/compositions may also be an omega-3 fatty acid, its ester of an edible fat/oil containing the same.

The other ingredient/additive/composition may contain mineral elements that provide health benefit. Such elements, for example may contain one or more of iron, magnesium, chromium or chromium derivatives, calcium and their derivatives such as chelated derivatives and like that which provide health benefits.

The additive ingredients may also be one or more of a vitamin.

The said additive may also be solvents that would improve solubilization of beneficial ingredients from other ingredients so that the bio-availability and efficacy of the components of the added ingredient increases. The solvents may include those that are permitted and acceptable food and/or pharmaceutical ingredients including, without limitation, edible oil, polar alcohols and polyols.

The said additive may also be excipients including, without limitation, flavors, sweeteners, preservatives including without limitation, polyols, high intensity artificial sweeteners and all known excipients and taste and flavor enhancers.

The additional ingredients may also be a mixture of the additional ingredients given above.

Given below are novel compositions of chlorophyllin. It is well known that the bioavailability of ingredients of natural products is markedly affected by the process of their preparation; and every change in the process results in a composition which has physical and bio-availability characteristics different than the earlier known process. The compositions and methods of preparing them disclosed below are illustrative and their obvious and equivalent variations are considered included within the scope of invention disclosed in this specification.

EXAMPLES

For all examples given below, commercially available Sodium Copper Chlorophyllin containing 302 mg copper per kg was used. However, other compositions containing reasonably lower and higher content of Sodium Copper Chlorophyllin can also be used to provide equivalent copper content in these compositions.

Example 1

(A) Composition 1:
Chlorophyll Composition Containing No Added Water
A composition was prepared by following steps:
To mixture of glycerol 6.25 kg and commercially available liquid sorbitol (which contains 30% water) 17.5 kg, 1.25 kg of commercially available sodium copper chlorophyllin composition containing 302 mg copper per kg was added; and mixed well.

(B) Case Studies on Patients:
  a. To a 13 years old girl having only one kidney was diagnosed for Chronic Kidney disease, She had edema all over her body and was unable to do her every-day activities. Serum creatinine level had reached 4 mg/dl. She was administered Composition 1 one spoon (12.5 g) two times a day for the first week and from second week onwards was administered one spoon a day. After one month serum creatinine level lowered to 1.4 mg/dl, edema had disappeared and her quality of life returned to normal.
  b. Composition 1 was consumed as a general health/wellness supplement by a diabetic patient of 64 years who had already undergone dialysis three times which brought down his serum creatinine level from 6 to 4.8. Later instead of dialysis this patient was administered Composition 1, one tea spoonful (12.5 ml) two times a day, once in morning on empty stomach and next in the evening. His serum creatinine level decreased after 11 days from 4.8 to 3.5. Five days later his serum creatinine was 2.6. This patient stopped taking this composition after the serum creatinine level came close to normal. This resulted in increase in serum creatinine level and accompanying discomfort returned again. Hence, this patient again resumed taking this composition, thereby again leading to drop in serum creatinine level.
  c. A patient aged 64 years suffering from diabetes and Chronic Kidney Disease had serum creatinine level of 7.7 mg/dl and hemoglobin 9.5 g/dl was administered Composition 1 one spoon (12.5 g) two times a day for the first week and from second week onwards, was administered one spoon a day. After one month serum creatinine level lowered to 6.2,mg/dl, hemoglobin increased to 9.9 g/dl. In the third month, serum creatinine level was 5 mg/dl and hemoglobin was 10 g/dl.
  d. In a woman of 27 years, diagnosed for Chronic Kidney Disease had serum creatinine level of 4.96 mg/dl and hemoglobin 6.5 g/dl was administered Composition 1 one spoon (12.5 g) two times a day for the first week and from second week onwards, was administered one spoon a day. After one month serum creatinine level lowered to 3 mg/dl, hemoglobin increased to 8 g/dl.
  e. A woman diagnosed for Chronic Kidney Disease had serum creatinine level of 4.33 mg/dl and hemoglobin 6.8 g/dl was administered Composition 1 one spoon (12.5 g) two times a day for the first week and from second week onwards, was administered one spoon a day. After one month serum creatinine level lowered to 3.7 mg/dl, hemoglobin increased to 8.5 g/dl. After second month creatnine lowered further to 3 mg/dl and hemoglobin increased to 8.9 g/dl.
  f. Following this experience, above the Composition 1 was prescribed to: (1) a group of patients having impaired kidney function but were not willing to go for dialysis for its high cost (Group 2 of Table 1), (2) to a group of patients in addition to the dialysis treatment two times per week; and data was kept at monthly intervals for hemoglobin, blood urea and serum creatinine (Group 1 of Table 1), and (3) concurrently, same data was also kept for a third group of patients that was purely on dialysis two times per week and to whom Composition 1 was never administered (Group 3 of Table 1). It was seen, surprisingly, that in Group 3 serum creatinine levels fluctuated and reduced in third month to some extent, however, in few patients for whom hemoglobin and blood urea results were available hemoglobin levels declined sharply in three months and blood urea levels also fluctuated. In comparison, there was a consistent decrease of serum creatinine in groups 1 and 2, with more decrease in group 2; and in few patients for whom hemoglobin and blood urea results were available in Groups 1 and 2, hemoglobin levels consistently increased after administration of Composition 1. Thus, positive contribution of the Composition 1 of this invention was seen in improving clinical parameters of kidney impaired patients. Since serum creatinine level results were available for all patients the results on serum creatinine were statistically analysed, which proved that the differences in serum creatinine levels of the three groups noted above are highly significant at $P=0.01$ Results and statistical analysis is given in table 1 below:

TABLE 1

Serum creatinine with and without dialysis and liquid chlorophyll composition 1 of the invention

| | Serial number of patient | Initial Serum creatinine mg/dl CRE | Serum creatinine after 30 days CRE | Serum creatinine after 60 days CRE |
|---|---|---|---|---|
| Treatment 1: Dialysis plus Liquid chlorophyll composition 1 | 1 | 7.7 | 6.2 | 5 |
| | 2 | 11 | 9.8 | 6.6 |
| | 3 | 4.9 | 3 | 2.8 |
| | 4 | 11.27 | 8.86 | 6.8 |
| | 5 | 4.35 | 3.8 | 2.3 |
| | 6 | 13.77 | 8.9 | 7.17 |
| | 7 | 7.8 | 6 | 5.3 |
| | 8 | 5.27 | 3.47 | 2.8 |
| | 9 | 9.3 | 5.16 | 3.16 |

TABLE 1-continued

Serum creatinine with and without dialysis and liquid
chlorophyll composition 1 of the invention

| Treatment | | | | |
|---|---|---|---|---|
| | 1 | 4 | 1.4 | 1 |
| 2: Liquid | 2 | 4.8 | 3.5 | 2.6 |
| chlorophyll | 3 | 3 | 2 | 1.8 |
| composition | 4 | 3.72 | 2.91 | 2.88 |
| 1; no | 5 | 4 | 3 | 1.8 |
| dialysis | 6 | 4 | 2.5 | 1.8 |
| | 7 | 4 | 2.3 | 1 |
| | 8 | 3 | 2.2 | 1.6 |
| | 9 | 5 | 3.6 | 1.8 |
| Treatment | 1 | 5.96 | 12.95 | 16.07 |
| 3: dialysis | 2 | 7.71 | 10.65 | 10.65 |
| only; no | 3 | 14.25 | 9.32 | 4.3 |
| liquid | 4 | 11.85 | 15.81 | 13.81 |
| chlorophyll | 5 | 14.2 | 5.92 | 4 |
| | 6 | 6.3 | 3.5 | 3.1 |
| | 7 | 5.5 | 3.1 | 7.2 |
| | 8 | 8.79 | 2.89 | 8.52 |
| | 9 | 9.2 | 13.3 | 2.8 |

TWO WAY ANALYSIS OF VARIANCE

| Source of variation | Degrees of freedom | Sum of squares | Mean Sum of Squares | F | P | Significance |
|---|---|---|---|---|---|---|
| Replicates | 8 | 244.1846 | 30.52308 | 1.826941 | 0.145 | Non-Significant |
| Treatment main | 2 | 452.7679 | 226.3839 | 13.55008 | 0.00036 | Very Highly Significant |
| Error a | 16 | 267.3153 | 16.70721 | | | |
| s sub-treatments | 2 | 732.5539 | 366.2769 | 17.10674 | 2.46E–06 | Very very highly significant |
| Interaction T × S | 4 | 112.0617 | 28.01542 | 1.308443 | 0.2804 | Non Significant |
| Error b | 48 | 1027.741 | 21.41126 | | | |
| Total | 80 | 2836.624 | | | | |
| Main treatments | | Treatments 1, 2, 3 = 1, 2, 3 months (T) | | | | |
| Sub-treatments | | Sub treatments: Initial Serum creatinine mg/dl, Serum creatinine after 30 days and Serum creatinine after 60 days Replications = 9 | | | | |

Example 2

Composition 2:

Following are illustrative chlorophyllin compositions comprising other ingredients supportive for kidney function added in the composition or forming a part of a kit containing the chlorophyllin composition To a mixture of glycerol 6.25 kg and commercially available liquid sorbitol (which contains 30% water) 17.5 kg, 0.32 kg of commercially available sodium copper chlorophyllin composition containing 302 mg copper per kg was added, 30 gram casein hydrolysate (80%) was added and mixed well.

Composition 2.1:

This composition comprises a kit comprising a bottle of Composition no. 1 and a bottle containing a composition comprising the "water insoluble high protein low fiber fraction" of Funugreek (*Trigonella foenum graecum* L.) and excipients. The "water insoluble high protein low fiber fraction", also known as leaf protein concentrate, is a high Biological Value protein concentrate, also further comprising natural beta carotene, xanthophylls, bioavailable iron and bio-available calcium in cell-free and highly bioavailable forms. Leaf protein concentrate is obtained by a process comprising steps of (i) comminuting fresh green crop material, (ii) separating a moist fibrous fraction as first primary fraction from the juice as second primary fraction, and (iii) treating the juice fraction to separate a water soluble deproteinized juice that is high in water content as third primary fraction from a water insoluble high protein low fiber fraction as fourth primary fraction. The instructions in the kit shall comprise consuming one teaspoonful of the Composition no. 1 in the morning at least 15 minutes to 30 minutes before consumption of tea or food; and consumption the composition containing the "water insoluble high protein low fiber fraction" with each major meal starting with breakfast.

Composition 3:

These compositions contained only sodium copper chlorophyllin as active ingredient.

Composition 3.1:

Sodium copper chlorohphyllin 5 gram was added to 95 gram glycerol. The composition was liquid with no appreciable colour, but the texture was smooth.

Composition 3.2:

Sodium copper chlorohphyllin 5 gram was added to 95 gram sorbitol. The composition was liquid with no appreciable colour, but the texture was smooth.

Composition 4:

Softgel of chlorophyllin Soft gel capsules were prepared containing following composition:

| Ingredient for a 500 mg soft gel capsule | Milligram |
|---|---|
| Sodium Copper Chlorophyllin (commercial powder containing copper 302 mg/kg) | 156 |
| Water | 50 |
| Glycerine | 10 |
| PEG 300 | 284 |
| Total | 500 |

The invention claimed is:

1. A method of treating a patient in need thereof suffering from kidney disease comprising administering a chlorophyllin composition in an amount effective for lowering the level of serum creatinine.

2. The method of claim 1, further comprising administering the chlorophyllin composition to achieve concurrent increase in blood hemoglobin level.

3. The method of claim 1, wherein the chlorophyllin composition is selected from the group consisting of sodium copper chlorophyllin, Potassium copper chlorophyllin, Potassium Iron chlorophyllin and other metal containing chlorophyllins, or a combination of two or more thereof.

4. The method of claim 2, wherein the chlorophyllin composition further comprises (a) a diluent, excipient or a carrier, or (b) no diluent, excipient or a carrier.

5. The method of claim 4, wherein the chlorophyllin composition further comprises (a) a second ingredient supportive for kidney function with the chlorphyllin composition as a first ingredient or provided in separate package as a part of kit comprising a package of the chlorophyllin composition and a package of the second ingredient, or (b) no second ingredient/composition supporting for kidney function.

6. The method of claim 4, wherein the chlorophyllin composition is selected from the group consisting of a liquid, powder, tablet or a capsule and the diluent, excipient or a carrier are selected from the group consisting of flavors, sweeteners, preservatives, polyols, taste and flavor enhancers.

7. The method of claim 6 wherein individual portion of the chlorophyllin composition comprises chlorophyllin, equivalent to 95% pure sodium copper chlorophyllin, 0.01 to 150 mg, and excipients; wherein the individual portion is 10 ml in case of a liquid composition, one gram in case of a powder composition, one tablet in case of tablet composition and one soft gelatin capsule in case of soft-gel composition.

8. The method of treating a patient according to claim 1, wherein the chlorophyllin composition comprising:
   a. a liquid composition comprising, per 12.5 gram portion of the chlorophyllin composition, chlorophyllin equivalent to 95% pure sodium copper chlorophyllin 0.01 to 150 mg, and
      at least one polyol, and
      0 to 3.75 gram of water; or
   b. a soft gelatin capsule comprising chlorophyllin equivalent to 0.1 to 1.5 milligram of 95% sodium copper chlorophyllin.

9. The method of claim 5, wherein the chlorophyllin composition is selected from the group consisting of a liquid, powder, tablet or a capsule.

10. The method of claim 9, wherein individual portion of the chlorophyllin composition comprises chlorophyllin, equivalent to 95% pure sodium copper chlorophyllin, 0.01 to 150 mg, and excipients; wherein the individual portion is 10 ml in case of a liquid composition, one gram in case of a powder composition, one tablet in case of tablet composition and one soft gelatin capsule in case of soft-gel composition.

11. The method of claim 7, wherein the chlorophyllin composition is 0.01 to 15 mg.

12. The method of claim 11, wherein the chlorophyllin composition is 0.01 to 0.2 mg.

13. The method of claim 8, wherein the chlorophyllin composition is 0.01 to 15 mg.

14. The method of claim 13, wherein the chlorophyllin composition is 0.01 to 0.2 mg.

15. The method of claim 10, wherein the chlorophyllin composition is 0.01 to 15 mg.

16. The method of claim 15, wherein the chlorophyllin composition is 0.01 to 0.2 mg.

* * * * *